United States Patent [19]

Aoyama et al.

[11] Patent Number: 6,060,628
[45] Date of Patent: May 9, 2000

[54] MANUFACTURING METHOD FOR 1,1,1,3,3-PENTAFLUOROPROPANE

[75] Inventors: Hirokazu Aoyama; Noriaki Shibata; Akinori Yamamoto, all of Settsu, Japan

[73] Assignee: Daikin Industries Ltd., Osaka, Japan

[21] Appl. No.: 08/894,694

[22] PCT Filed: Feb. 8, 1996

[86] PCT No.: PCT/JP96/00273

§ 371 Date: Aug. 26, 1997

§ 102(e) Date: Aug. 26, 1997

[87] PCT Pub. No.: WO96/26914

PCT Pub. Date: Jun. 9, 1996

[30] Foreign Application Priority Data

Feb. 28, 1995 [JP] Japan ..................................... 7-065159

[51] Int. Cl.[7] .............................. C07C 19/08; C07F 15/00
[52] U.S. Cl. ........................... 570/134; 556/136; 570/176
[58] Field of Search .................................... 570/176, 134; 556/136

[56] References Cited

U.S. PATENT DOCUMENTS

| 5,243,105 | 9/1993 | Scott et al. | 510/165 |
| 5,659,093 | 8/1997 | Takubo et al. | 570/167 |

FOREIGN PATENT DOCUMENTS

| 0 611 744 | 8/1994 | European Pat. Off. . |
| 62-77338 | 4/1987 | Japan . |
| 94/14736 | 7/1994 | WIPO . |

Primary Examiner—John Kight
Assistant Examiner—Charanjit S. Aulakh
Attorney, Agent, or Firm—Armstrong, Westerman, Hattori, McLeland & Naughton

[57] ABSTRACT

A manufacturing method for 1,1,1,3,3-pentafluoropropane in which the method is composed of:

step A wherein 2,3-dichloro-1,1,1,3,3-pentafluoropropane is reduced with hydrogen under the presence of hydrogenation catalyst in gaseous phase;

step B wherein all of the products of the said step A are introduced into a cooler condenser, so that either a component of hydrogen and hydrogen chloride as non-condensation component and another component of 1,1,1,3,3-pentafluoropropane as condensation components or a component of hydrogen as non-condensation component and another component of hydrogen chloride and 1,1,1,3,3-pentafluoropropane as condensation component are obtained;

step C wherein hydrogen is separated from the non-condensation component of the said step B, and it is recycled to the said step A; and step D wherein 1,1,1,3,3-pentafluoropropane is separated from the condensation component of the said step B.

The producing method based on a manufacturing process of 1,1,1,3,3-pentafluoropropane can be provided with good efficiency and economy in industrial scales.

14 Claims, No Drawings

MANUFACTURING METHOD FOR 1,1,1,3,3-PENTAFLUOROPROPANE

This application is a 371 of PCT/JP 96/00273, filed Feb. 8, 1996 now WO 96/26914 published Jun. 9, 1996.

INDUSTRIAL FIELDS WHERE THE INVENTION CAN BE UTILIZED

This invention relates to a manufacturing method for 1,1,1,3,3-pentafluoropropane which is a useful compound that can be substituted for CFC and HCFC to be used as a cooling medium, a blowing agent, and a cleaning agent.

PRIOR ART

As a manufacturing method for 1,1,1,3,3-pentafluoropropane, it is known that 2,3-dichloro-1,1,1,3,3-pentafluoropropane and 2,2,3-trichloro-1,1,1,3,3-pentafluoropropane as raw materials are reduced with hydrogen by using a palladium catalyst supported by active carbon etc.(see the Japanese Patent Opening No. 256235/94).

However, the said known reference does not disclose the process for producing 1,1,1,3,3-pentafluoropropane with good efficiency and economy on an industrial scale.

OBJECTIVES OF THE INVENTION

The object of this invention is to provide a manufacturing method based on a process of producing 1,1,1,3,3-pentafluoropropane with good efficiency and economy on an industrial scale.

THE CONSTRUCTION OF THE INVENTION

As a result of closely studying a manufacturing method for 1,1,1,3,3-pentafluoropropane with good efficiency and economy on an industrial scale, the inventors found that 2,3-dichloro-1,1,1,3,3-pentafluoropropane as a raw material is reduced with hydrogen through gaseous-phase reaction under the presence of a hydrogenation catalyst at not less than the atmospheric pressure, resulting reaction products are introduced into a condenser in which component composed of hydrogen and hydrogen chloride as non-condensation component and component composed of 1,1,1,3,3-pentafluoropropane as a condensation component are obtained, and 1,1,1,3,3-pentafluoropropane is separated from the condensation component so as to obtain it with high yield. Besides, they found that hydrogen is separated from the component composed of hydrogen and hydrogen chloride which are obtained as the non-condensation component and recycling this hydrogen to said reduction reaction results in no loss of hydrogen and high improvement of economy. Thus, the present invention has been accomplished.

That is, the present invention relates to a manufacturing method for 1,1,1,3,3-pentafluoropropane comprising:

step A wherein 2,3-dichloro-1,1,1,3,3-pentafluoropropane is reduced with hydrogen under the presence of hydrogenation catalyst in gaseous phase;

step B wherein all of the products of the said step A are introduced to a cooler condenser, so that either a component composed of hydrogen and hydrogen chloride as non-condensation component and another component composed of 1,1,1,3,3-pentafluoropropane as condensation component are obtained, or a component composed of hydrogen as non-condensation component and another component composed of hydrogen chloride and 1,1,1,3,3-pentafluoropropane as condensation component are obtained;

step C wherein hydrogen is separated from the non-condensation component of the said step B, and it is recycled to the said step A; and step D wherein 1,1,1,3,3-pentafluoropropane is separated from the condensation component of the said step B.

In a manufacturing method of the present invention, as for the hydrogenation catalyst used in the step A, though the known catalysts having the hydrogenation ability can be used, preferably, the catalyst composed of palladium is preferable.

As for the catalyst composed of palladium, it can be solely palladium, or it can be added by other metals for improving the ability of acid-resistance or preventing it from sintering. As these additive metals, there are exemplified at least one metal selected from the group of silver, gold, copper, tellurium, zinc, chromium, rhenium, cobalt, nickel, iridium, ruthenium, rhodium, tantalum, niobium, molybdenum, osmium and tungsten, and so on.

A ratio of the additive metals to the palladium is from 0.01 to 100% by weight, preferably from 0.1 to 30% by weight.

A preparing method can be the known preparing method for hydrogenation catalyst. For example, the method can be given in which after an aqueous solution of the salt containing the component of the catalyst or an aqueous solution added by hydrochloric acid is impregnated to the carrier, it can be dried and reduced with hydrogen etc.

As the carrier for the hydrogenation catalyst used in the present invention, at least one selected from the group of active carbon, alumina, silica gel, titanium oxide and zirconia is applied. Particularly, active carbon is preferable because 1,1,1,3,3-pentafluoropropane as an objective material can be obtained with high selectivity.

Although having little effect on the reaction, the particle size of the carrier is preferably from 0.1 to 100 mm.

As for the concentration of the catalyst supported on the carrier, althogh a wide range from 0.05 to 30% by weight can be used, ordinally from 0.05 to 10% by weight, preferably 0.5 to 5% by weight is recommended.

The temperature of gaseous phase reaction is usually from 100 to 350° C., preferably from 200 to 300° C.

The gaseous phase reaction can be a fixed-bed gaseous phase reaction and fluidized-bed gaseous phase reaction etc.

In the reduction reaction of 2,3-dichloro-1,1,1,3,3-pentafluoropropane with hydrogen, the ratio of hydrogen to the raw material can be changed widely as long as the hydrogen amount is not less than the stoichiometric amount for 2,3-dichloro-1,1,1,3,3-pentafluoropropane.

However, the hydrogenation is usually carried out by using hydrogen in an amount of 1.5 to 5 times as large as the stoichiometric amount, that is, in an amount of 3 to 10 times mol, preferably from 3 to 6 times mole for 2,3-dichloro-1,1,1,3,3-pentafluoropropane. To the total mole of the starting material, a considerably excessive moles of hydrogen than the stoichiometric amount, for example, 10 or more moles can be used. Hydrogen needs to be recycled because not less than the stoichiometric amount of hydrogen is usually used.

Though the reaction pressure is not restricted particularly, the pressure ranging from 0 to 25 Kg/cm²G can be preferably applied. Even at a higher pressure than the range the reaction can proceed, but the apparatus enough to bear the high pressure is required so that the cost of the equipments may be high.

The contact time is usually from 0.1 to 300 seconds, particularly from 1 to 30 seconds.

2,3-dichloro-1,1,1,3,3-pentafluoropropane as a raw material is the known compound, and this can be produced by fluorination of perchloropropene (refer to E. T. McBEE, ANTHONY TRUCHAN, R. O. BOLT, J.Amer.Chem.Soc., vol.70, 2023–2024(1948)).

In a manufacturing method of the present invention, the step A can be carried out continuously.

And, though the temperature of the condenser in the step B can be the most suitable value according to the reaction condition etc., the temperature from −40° C. to 80° C., preferably from −20° C. to 60° C., more preferably from −10° C. to 40° C. can be given. A form of the condenser is not restricted, for example, the condenser having a tower can be used.

As for the pressure in the step B, the pressure in the step A can be maintained without changing, when necessary, after raising with the compressor etc. it can be introduced to the step B.

In the step B, ordinarily, the non-condensation component can be taken out from the upper portion of the the condenser in gaseous form while the condensation component can be taken out from the lower portion of the condenser in liquid form.

The step B can also be carried out continuously.

And, as for the separating method for hydrogen in the step C, various kinds of methods can be applied. When the non-condensation component obtained in the step B is composed of hydrogen, it can be recycled to the step A as it is, and also it can be recycled to the step A after removing hydrogen chloride contained in a little amount, for example, by rinsing with alkaline water, and then drying.

When the non-condensation component obtained in the step B is composed of hydrogen and hydrogen chloride, after removing hydrogen chloride contained, for example, by rinsing with alkaline water, and then drying, thus separated hydrogen can be recycled to the step A. Also, after hydrogen is separated as the non-condensation component with condensing the hydrogen chloride by cooling etc., it can be recycled to the step A. In this case, the operation is preferably conducted with the pressure raised by a compressor.

Also, the step C can be carried out continuously.

Furthermore, as for the separating method for 1,1,1,3,3-pentafluoropropane from the condensation component in the step B, the separating method by rectification can be generally applied, and it can be carried out by batch method or continuous method.

THE POSSIBILITY OF UTILIZING THE INVENTION IN INDUSTRY

The manufacturing method of the present invention, comprises:

step A wherein 2,3-dichloro-1,1,1,3,3-pentafluoropropane is reduced with hydrogen under the presence of a hydrogenation catalyst by way of gaseous phase reaction at not less than the atmospheric pressure;

step B wherein all of the products of the said step A are introduced into a cooler condenser, so that either the component of hydrogen and hydrogen chloride as the non-condensation component and the component of 1,1,1,3,3-pentafluoropropane as the condensation component are obtained, or the component of hydrogen as the non-condensation component and the component of hydrogen chloride and 1,1,1,3,3-pentafluoropropane as the condensation component are obtained;

step C wherein hydrogen is separated from the non-condensation component of the said step B, and it is recycled to said step A; and step D wherein 1,1,1,3,3-pentafluoropropane is separated from the condensation component of the said step B.

Accordingly, 1,1,1,3,3-pentafluoropropane can be obtained with good efficiency and economy on an industrial scale.

EMBODIMENTS

This invention will be explained in more detail through the following examples.

EXAMPLE 1

Concerning the Steps A and B 5.12 g of palladium catalyst carried on active carbon in a concentration of 3% by weight were filled into a reactor tube made of SUS-316 of 20 mm inside diameter and 400 mm length which had a perforated plate at the center and an inner tube for a thermoelectric thermometer, and nitrogen gas was flowed through the tube at 40 cc/min for 2 hours. Next, while hydrogen gas replaced with nitrogen gas was flowed at the same rate, the tube was heated in an electric furnace at 250° C. and kept for 2 hours.

80 cc/min of hydrogen gas and 20 cc/min of 2,3-dichloro-1,1,1,3,3-pentafluoropropane were flowed through the tube under the atmospheric pressure. Heating from outside was controlled to keep the reaction temperature at 250° C.

When the gas from the tube outlet under the atmospheric pressure was introduced into a condenser cooled at −5° C., a component containing hydrogen and hydrogen chloride as non-condensation component and another component composed of 1,1,1,3,3-pentafluoropropane as condensation component were obtained.

As a result of analysis for the gas from the tube outlet by gas chromatography, the conversion was 100% and the selectivity was 97.5%.

EXAMPLE 2

Concerning the Steps A and B

A catalyst of palladium carried on active carbon in a concentration of 3% by weight was impregnated into an aqueous solution where silver nitrate was dissolved so that silver as metal component would be 10% by weight to palladium. After removing water under reduced pressure, it was further dried at 120° C. for 5 hours.

Next, the catalyst was filled into a reactor tube made of SUS-316, and after it was further dried with flowing nitrogen gas at 300° C. for 5 hours, hydrogen gas was introduced at the same rate and the catalyst was reduced by keeping it for 5 hours.

Using 5.10 g of the catalyst obtained by this process, the reaction was carried out as Example 1 under the pressure of 2 kg/cm$^2$G. While keeping the gas from the tube outlet at 2 kg/cm$^2$G, it was introduced into a condenser cooled at 0° C., so that a component containing hydrogen and hydrogen chloride as non-condensation component and another component composed of 1,1,1,3,3-pentafluoropropane as condensation component were obtained.

As a result of analysis for the gas from the tube outlet by gas chromatography, the conversion was 99% and the selectivity was 96%.

EXAMPLE 3

Concerning the Step C

The non-condensation component composed of hydrogen and hydrogen chloride obtained in Example 1 was introduced into a rinsing tower, and further introduced into an alkaline rinsing tower using a 10% aqueous solution of NaOH to remove hydrogen chloride. Hydrogen obtained was dried by successively passing through drying tubes filled with calcium chloride, and Molecular Sieves.

When the step A was conducted by using thus recovered hydrogen and newly adding hydrogen for shortage amount, the reaction was proceeded without problems.

EXAMPLE 4

Concerning the Step D

The condensation component composed of 1,1,1,3,3-pentafluoropropane obtained in Example 1 was rectified by oldershow type rectification tower (15 layers) under the atmospheric pressure. Temperature of a condenser used was −10° C. 1,1,1,3,3-pentafluoropropane having 15° C. of boiling point was obtained with a purity of not less than 99.5%.

EXAMPLE 5

The reaction as mentioned in Example 1 was carried out under 5 kg/cm$^2$G of the reaction pressure. While the gas from the tube outlet was kept at 5 kg/cm$^2$G of pressure, it was introduced into a condenser cooled at −70° C., so that a component containing hydrogen as non-condensation component and another component composed of hydrogen chloride and 1,1,1,3,3-pentafluoropropane as condensation component were obtained.

As a result of analysis for the gas from the tube outlet by gas chromatography, the conversion was 98.5% and the selectivity was 95.5%.

We claim:

1. A process for producing 1,1,1,3,3-pentafluoropropane comprising:
    step A wherein 2,3-dichloro-1,1,1,3,3-pentafluoropropane is reduced with hydrogen in gaseous phase under the presence of hydrogenation catalyst comprising palladium;
    step B wherein all of the products of the said step A are introduced into a cooler condenser, so that a component composed of hydrogen and hydrogen chloride as non-condensation component and another component composed of 1,1,1,3,3-pentafluoropropane as condensation component are obtained;
    step C wherein hydrogen is separated from the non-condensation component of the said step B, and it is recycled to the said step A; and
    step D wherein 1,1,1,3,3-pentafluoropropane is separated from the condensation component of the said step B.

2. A process as defined by claim 1, where hydrogen is used in 3 to 10 times mole to 2,3-dichloro-1,1,1,3,3-pentafluoropropane.

3. A process as defined by claim 1, where base catalyst of palladium carried on active carbon is used as the hydrogenation catalyst.

4. A process as defined by claim 3, where the concentration of the palladium to the active carbon as a carrier is from 0.05 to 10% by weight.

5. A process as defined by claim 1, where the reaction of the step A is carried out at the temperature ranging from 100 to 350° C.

6. A process as defined by claim 1, where the reaction of the step A is carried out under the pressure ranging from 0 to 25 kg/cm$^2$G.

7. A process as defined by claim 1, where an apparatus for raising pressure is set up between the step A and the step B.

8. A process for producing 1,1,1,3,3-pentafluoropropane comprising:
    step A wherein 2,3-dichloro-1,1,1,3,3-pentafluoropropane is reduced with hydrogen in gaseous phase under the presence of hydrogenation catalyst comprising palladium;
    step B wherein all of the products of the said step A are introduced into a cooler condenser, so that a component composed of hydrogen as non-condensation component and another component composed of hydrogen chloride and 1,1,1,3,3-pentafluoropropane as condensation component are obtained;
    step C wherein hydrogen is separated from the non-condensation component of the said step B, and it is recycled to the said step A; and
    step D wherein 1,1,1,3,3-pentafluoropropane is separated from the condensation component of the said step B by rectification.

9. A process as defined by claim 8, where hydrogen is used in 3 to 10 times mole to 2,3-dichloro-1,1,1,3,3-pentafluoropropane.

10. A process as defined by claim 8, where base catalyst of palladium carried on active carbon is used as the hydrogenation catalyst.

11. A process as defined by claim 10, where the concentration of the palladium to the active carbon as a carrier is from 0.05 to 10% by weight.

12. A process as defined by claim 8, where the reaction of the step A is carried out at the temperature ranging from 100 to 350° C.

13. A process as defined by claim 8, where the reaction of the step A is carried out under the pressure ranging from 0 to 26 kg/cm$^2$G.

14. A process as defined by claim 8, where an apparatus for raising pressure is set up between the step A and step B.

* * * * *